United States Patent [19]
Powell

[11] 3,936,273
[45] Feb. 3, 1976

[54] APPARATUS FOR DETERMINING THE CORROSION PROTECTION PERFORMANCE OF A FLUID

[75] Inventor: Donald L. Powell, Chicago, Ill.

[73] Assignee: Autoresearch Laboratories, Inc., Chicago, Ill.

[22] Filed: Feb. 25, 1974

[21] Appl. No.: 445,468

[52] U.S. Cl.............................. 23/253 C; 23/230 C
[51] Int. Cl.².................................... G01N 31/00
[58] Field of Search....................... 23/230 C, 253 C

[56] References Cited
UNITED STATES PATENTS
2,897,060 7/1959 Dieman........................... 23/230 C
3,116,977 1/1964 Grabowski et al................ 23/253 C OTHER PUBLICATIONS
Chandler, "Testing Ferrous metals for Corrosion Resistance", British Iron & Steel Research Ass., London 1961, pp.13–15.
Champion, "Corrosion Testing Procedures", Wiley & Sons Inc., New York, 1964 pp. 66–82, 118–128, 404–405, 101–107.
ASTM Standards 1965, Part 3, pp. 164–172.

Primary Examiner—Joseph Scovronek
Assistant Examiner—Arnold Turk
Attorney, Agent, or Firm—Hume, Clement, Brinks, Willian, Olds & Cook, Ltd.

[57] ABSTRACT

A test apparatus for determining the corrosion protection performance of fluids includes a housing, an axial shaft mountable therein, a heating element, and a drive motor. The housing which contains the test fluid is preferably sealable to maintain a predetermined environment therein. The housing also includes a port or ports for introduction of corrosion initiating substances. The heating element is adjacent to a lower portion of the housing to provide increased temperatures within the housing when desired. Test specimens are mounted on the shaft and may be rotated in partially immersed emplacement within the bath.

The process for determining the corrosion protection performance of a fluid comprises forming a bath of the test fluid and rotating a partially immersed, substantially corrosion free test specimen therein in the presence of a corrosive environment. Thereafter the specimen may be maintained in static and partially immersed emplacement within the bath. After a sufficient processing period the specimen is examined to determine the degree of corrosion thereon.

4 Claims, 2 Drawing Figures

APPARATUS FOR DETERMINING THE CORROSION PROTECTION PERFORMANCE OF A FLUID

FIELD OF THE INVENTION

The present invention relates to an apparatus and method for evaluating the corrosion protection performance of fluids. More particularly, the present invention is directed toward an apparatus and method for evaluating the moisture corrosion protection performance of lubricating oils as, for example, automotive gear lubricants.

BACKGROUND OF THE INVENTION

The corrosion of machine components in the presence of moisture and other corrosive substances is an important cause of mechanical system failures. One of the widely used means of controlling or preventing this corrosion is to employ the corrosion preventing properties of the lubricants, fuels, and functional fluids (for example, hydraulic brake fluids) used in the system. The rust preventing properties of lubricants, fuels and functional fluids can be enhanced by the addition of chemical additives. In order to determine the performance of these fluids in preventing the corrosion of machine elements a wide number of tests have been devised and have been used by industry. Some of the most widely used tests are described hereinbelow.

The Humidity Cabinet Test (ASTM D-1748) evaluates the ability of the test lubricant or other coating to protect a specially prepared steel specimen from rusting when stored in a chamber at an elevated temperature in air substantially saturated with water vapor.

The Turbine Oil Rust Test (ASTM D-6665) evaluates the corrosion characteristics of a fluid on a cylindrical steel sample while the sample is submerged in a constantly stirred mixture of the test fluid in water.

The Test for Corrosiveness and Oxidation Stability of Light Oils (Federal Test Method 5308) evaluates the corrosion of coupons of several metals while immersed in a sample of oil which is heated and aerated continuously.

The Test for Corrosion of Lead by Lubricating Oils (Federal Test Method 5321) employs the immersion of lead samples in the presence of a copper catalyst in heated test oil with continuous aeration in order to determine corrosion protection performance.

These and several other similar methods measure the ability of the test oil to prevent corrosion in either a totally liquid or totally vapor phase environment. None of the foregoing tests, however, have proven to produce results or data which correlate with the test which is generally accepted as the standard within the industry for measuring the corrosion protection performance of automotive gear lubricants (The Coordinating Research Counsel L-33 Moisture Corrosion Test).

The CRC L-33 Test is a method for measuring the moisture corrosion protection of lubricating oils which is both time-consuming (about 7 days) and physically cumbersome to perform (the entire automotive rear axle is employed in carrying out the testing procedure). Thus, there is a need in the lubricating materials art for a test procedure which may be expeditiously performed, which utilizes small test specimens and small amounts of test fluids, and which furthermore correlates to the CRC L-33 moisture corrosion test.

SUMMARY OF THE INVENTION

The present invention is directed toward a method and apparatus for determining the corrosion protection performance of various fluids. The test is of relatively short duration and uses small test samples. Moreover, the results obtained through the implementation of the apparatus and process of the present invention appear to correlate with the CRC L-33 Moisture Corrosion Test which is presently employed by the federal government for the qualification of automotive gear lubricants.

Generally, the method of the present invention comprises the steps of forming a bath of the fluid to be tested; rotating a specimen partially immersed in said bath for a predetermined period of time, the specimen being initially substantially free of corrosion; subjecting the specimen to a corrosion initiating substance during at least a portion of said rotation period; removing the specimen from said bath; and determining the degree of corrosion of said specimen. The specimen may also be maintained in static and partially immersed emplacement within said bath for a second predetermined period of time subsequent to said rotation period and prior to removing the specimen from the corrosive environment.

The apparatus contemplated by the present invention includes a housing for containing the test fluid; means for mounting a test specimen within said housing; means for rotating said mounting means with the test specimen mounted thereon; means for heating said fluid within said housing and means for regulating the temperature of said fluid therein; and said housing including a sealable port means for introducing into said housing a corrosion initiating substance.

The foregoing method and apparatus may use a variety of test specimen made of different materials, test fluids and corrosion initiating substances. Therefore, the corrosion prevention properties of the test fluid or lubricant may be evaluated within an environment which simulates that of a variety of machines or mechanical systems.

BRIEF DESCRIPTION OF THE DRAWINGS

The novel features which are believed to be characteristic of the invention are set forth in the appended claims. The invention itself, however, together with further objects and attendant advantages thereof, will be best understood by reference to the following description taken in connection with the accompanying drawings, in which:

DETAILED DESCRIPTION OF THE INVENTION

Figure 1:
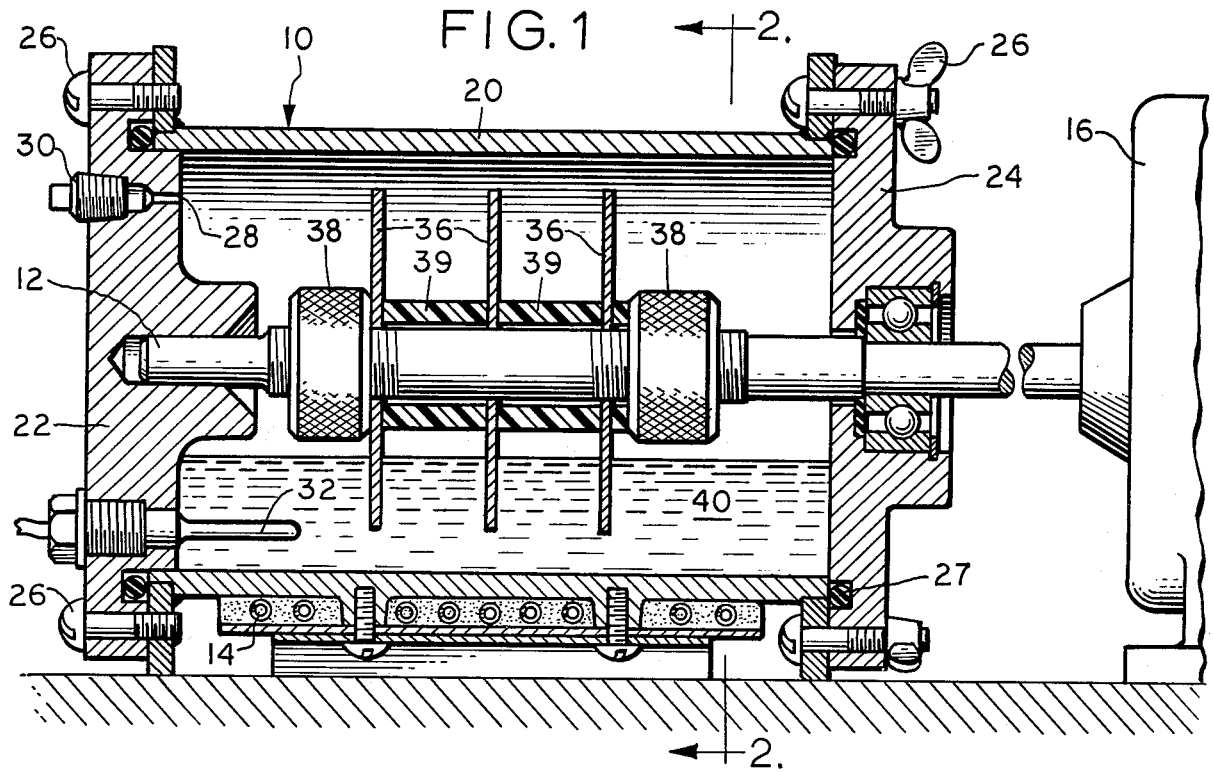
FIG. 1 is a side elevational view of the apparatus of the present invention in partial section for clarification.

Referring now to FIG. 1, the test apparatus of the present invention includes a housing, designated generally as 10, a shaft 12 mounted within the housing 10 and axially extending therein, a heating element 14 which is disposed adjacent to the lower portion of the housing 10, and a motor 16 which detachably engages shaft 12 and rotates the same within the housing 10.

The housing 10 includes a lateral wall 20 and two endwalls, 22 and 24 respectively. While the housing 10 may be composed of various materials, it is preferred that materials be utilized which are immune to corrosion by the corrosion initiating substance which is employed in the test method. These materials are preferred since corrosion on the interior surfaces of the housing 10 would retain moisture and test fluids from previous test runs and thereby contaminate and adversely affect subsequent test runs. Thus, the use of corrosion free materials insures uniformity in testing. Of course, the particular materials to be used will be dependent upon the particular corrosion initiating substance. For example, in testing the ability of gear lubricants to protect ferrous metals from water corrosion nickel or chrome plated steel, stainless steel or plastic have been found to be suitable.

While different modes of construction will occur to those skilled in the art, it is preferred for ease in cleaning that the lateral wall 20 and endwalls 22 and 24 be capable of disassembly. As can be seen in FIG. 1, endwalls 22 and 24 are removably secured to lateral wall 20 by suitable fastening means, as for example bolts 26. Suitable sealing means, as for example gaskets or O-rings 27, are also employed within endwalls 22 and 24 so as to maintain the endwalls in sealed engagement with lateral wall 20. This arrangement insures that the environment maintained within the housing 10 will not be contaminated. Of course, any well known means may be employed in the endwalls 22 and 24 to support the shaft 12. The endwall 22 also includes a small aperture or port 28 in its upper portion which is utilized to introduce into the housing 10 a corrosion initiating substance. The aperture 28 may include a self-sealing penetrable diaphragm which maintains the environment within the housing 10 free of contamination and through which a syringe may be inserted to introduce a corrosion initiating substance. Alternatively, aperture 28 may be provided with a suitable closing means, as for example pipe plug 30, which sealably closes aperture 28 before and after the introduction of the corrosion initiating substance.

As is also shown in FIG. 1, a means 32 for measuring the temperature of the test fluid is mounted within the lower portion of the housing 10. The temperature sensing means 32, for example a thermocouple or other temperature sensing transducer, is connected to a temperature controller 34 which modulates the heat generated by heating element 14. In this manner the apparatus of the present invention may accurately simulate the temperature of the machine environment in which the test fluid and test specimen materials are to be used. If desired, a plurality of test specimens 36 may be simultaneously employed. The specimens 36 are mounted on the rotatable shaft 12 within the housing 10 wherein they are subjected to corrosive attack. Threaded collars 38 and spacing elements 39 can be utilized to maintain the test specimens 36 in fixed and space emplacement, thereby permitting free flow of vapor and liquid there between. For the reasons mentioned above, it is also desirable that the shaft 12, the collars 38, and spacers 39 be made of a non-corrosive material.

The apparatus described hereinabove can be advantageously utilized in the process of the present invention. This process provides a relatively short and accurate means for determining the corrosion protection performance of various fluids.

In accordance with the process, the apparatus is first thoroughly cleaned with a dry-cleaning naptha and rinsed with a suitable solvent such as n-pentane.

The test specimens 36 are then mounted on the rotatable shaft 12 and assembled into position within the housing 10 as is shown in FIG. 1.

It is, of course, preferable that the surfaces of the test specimens be initially substantially free of corrosion. Therefore, the test specimens should be subjected to mechanical cleaning action, as for example by sand blasting, prior to use. Moreover, since the degree of surface roughness of the test specimens 36 has an influence upon the rate of corrosion, it is important that a particular mechanical cleaning process be used consistently throughout a given series of tests. It is recommended that sand blasting be performed at an air pressure of about 90 psi and that a sand having 99.8% silicon dioxide with a moh hardness number 7 and an American Foundryman's Society grain fineness number 26 be employed (Wedron Sand No. 4098, Wedron Silicon Co., Chicago, Ill.). Subsequent to mechanical cleaning the test specimen should be thoroughly washed in dry-cleaning naptha, rinsed with a suitable solvent such as n-pentane and air dried. With the use of forceps the test specimens should be immersed in a small sample of the fluid to be tested so that all surfaces are coated. This tends to arrest premature corrosion of the sample. After allowing the excess fluid to drain from the specimens they are assembled on shaft 12 with elements 39 and collars 38 utilized to maintain the specimens in a spaced and fixed position. The entire test specimen and shaft assembly are then mounted within the housing 10.

Figure 2:
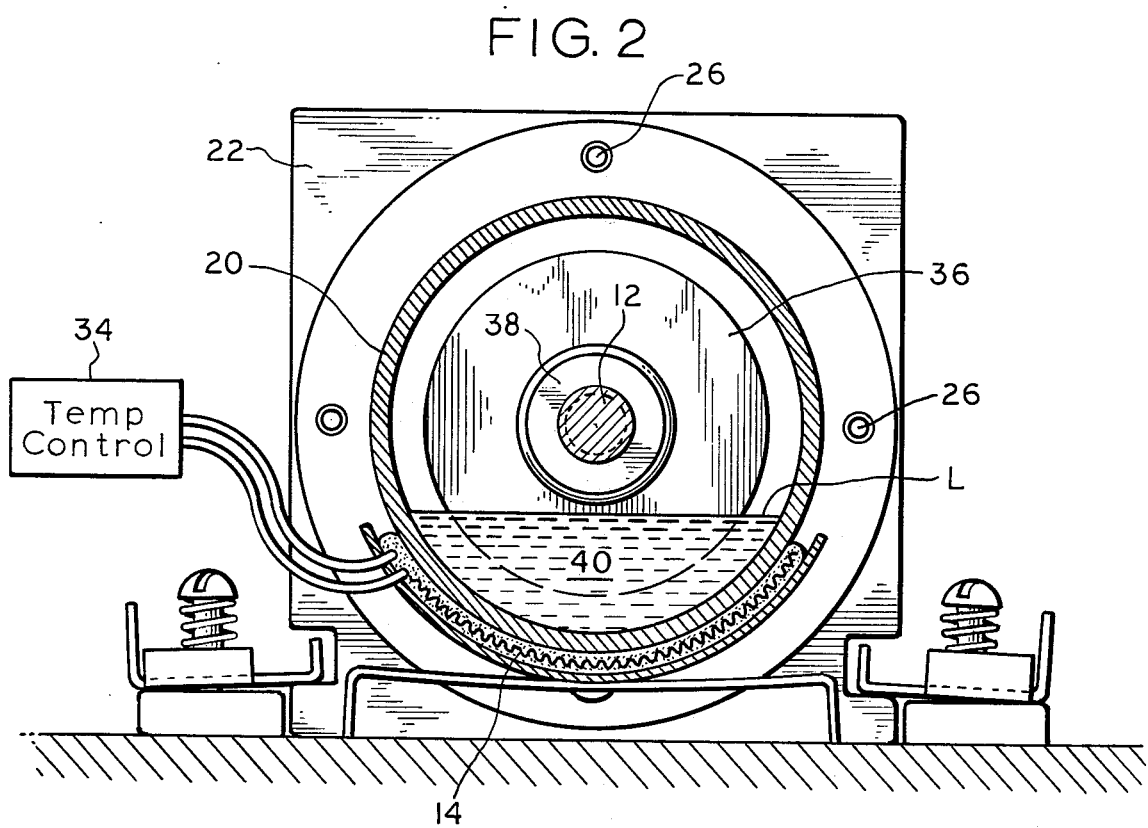
FIG. 2 is a cross-sectional view of the apparatus taken along line 2—2 of FIG. 1.

A bath of the test fluid, designated as 40 in FIG. 2, is formed in the lower portion of the housing 10 and is provided in an amount sufficient to bring the level L of the test fluid to a point just below the threaded collars 38 and spacing elements 39. The test fluid can be placed within the housing 10 before the endwall 24 is assembled, or alternatively, a sealable port, suitably located, may be employed to introduce the test fluid into the housing 10, after the assembly of endwall 24 to lateral wall 20.

From this point forward it is preferable to maintain the interior of the housing 10 substantially sealed from the external environment in order to assure uniform test parameters.

After connecting the drive motor 16 onto shaft 12 the test specimens are initially rotated while partially immersed in the test fluid for a time sufficient to thoroughly wet the surfaces of the test specimens with the test fluid. This insures that no corrosion initiating substance will contact an uncoated specimen. In testing automotive gear lubricants with ferrous metal test specimens it has been found that an initial rotation period of between about 5 to 30 minutes is suitable for adequately wetting the test specimen surfaces. At this point the corrosion initiating substance is introduced into the housing 10 through aperture 28 and the rotation period is continued for an additional time sufficient to allow adequate mixing of the test fluid and the corrosion initiating substance and the development of an environment which simulates that of a given machine. The amount of corrosion initiating substance employed for a particular test will of course vary so as to simulate the machine environment in which the fluid and specimen are to be used. For example, automotive gear lubricants are tested to determine their ability to protect metals from oxidation corrosion in the presence of water. Accordingly, it has been found that in such tests water should be introduced into the housing 10 in an amount equal to about 1–5% of the test lubricant by volume. It has been found, further, that in testing automotive gear lubricants with ferrous metal specimens the rotation period should be continued for about 30 minutes subsequent to the introduction of the water through aperture 28.

Oftentimes it is necessary to heat the bath 40 in order to develop the appropriate environment within the housing 10. Thus, during the rotation period the heating element 14, the temperature sensing device 32 and temperature controller 34 are employed to provide within the housing 10 the temperature which is considered appropriate for the particular test. When testing automotive gear lubricants with ferrous metal specimens it has been found that a temperature of approximately 180°F is desirable to activate the chemical additives of the test fluid and also to vaporize a portion of the corrosion initiating substance, in this case water, in order to provide a liquid and vapor phase corrosive environment.

Having run the rotation period for a predetermined length of time found suitable for the particular test, the motor 16 is turned off and the test specimen 36 is maintained in static and partially immersed emplacement within bath 40 for a second predetermined period of time. In this manner a simultaneous test is made for both liquid and vapor phase environments. The stationary period of the test is preferably of sufficient length to allow the corrosion mechanism to progress to the point where corrosion will be ascertainable by visual inspection. For example, when testing automotive gear lubricants with ferrous metal specimens, it has been discovered that at least about 5 hours are necessary to identify corrosive action on the specimen and preferably about 20 hours are employed for the stationary period. This longer period allows for overnight testing and insures adequate corrosive action on the specimen to insure accurate and consistent data.

It is also preferably to maintain the corrosion initiating substance in intimate association with the test specimen during the stationary period. Accordingly, at least some of the vapor generated during the rotation period may be condensed onto the specimens 36 by cooling the bath 40 through adjustment of the temperature controller 34. For example, the temperature of the bath 40 should be lowered to about 125°F during the rotation period when testing automotive gear lubricants with ferrous metals.

At the termination of the stationary period the test specimen 36 is removed from the housing 10 and the shaft 12. Care should be taken not to disturb or remove the corrosion which has developed, and it is desirable, therefore, to use forceps to handle the specimen.

Finally, the test fluid is rinsed from the specimen with a suitable solvent and a determination is made as to the degree of corrosion. The examination of the specimen can be made by visual inspection, with or without auxiliary optical equipment, or by other means capable of detecting and measuring corrosion or chemical degradation. Generally, the data is reported as a percentage of the total specimen area covered by the corrosion, both above and below the test fluid level.

Of course, it should be understood that various modifications may be made to the preferred embodiments disclosed herein without departing from the spirit and scope of the present invention. For example, corrosion protection is not limited to the arrest or impedence of ferrous oxidation but is intended to include other forms of chemical degradation. Likewise, the apparatus and method disclosed herein is not intended to be limited to particular test fluids, test specimens, or corrosion initiating substances. Thus, the test specimen may include metals, wood, plastic, and the like; while the corrosion initiating substance may be in liquid, vapor or solid form.

Other modes of applying the principles described herein are intended to fall within the scope of the invention provided the features stated in any of the following claims or the equivalent of such be employed.

I claim:

1. An apparatus for determining the corrosion protection performance of a fluid comprising:
   a sealably encloseable and disassemblable housing, said fluid being contained therein;
   means for mounting test specimens, said mounting means including a shaft, means for axially spacing a plurality of test specimens on said shaft and collar means which engage said shaft and maintain said specimens in fixed position thereon, said mounting means disposed within said housing and in spaced relation with the bottom thereof such that said test specimens may be partially immersed in the liquid phase of said fluid;
   means for rotating said mounting means with said specimens mounted thereon;
   means for regulating the temperature of said fluid and including a heating element positioned externally of, adjacent to and abutting a lower portion of said housing; and
   sealable port means disposed in said housing for introducing into said housing a corrosion initiating substance.

2. The apparatus of claim 1 wherein said housing includes a cylindrical lateral wall and a pair of end walls, and wherein said temperature regulating means includes a temperature sensing component which is mounted on one of said end walls and extends into an internal lower portion of said housing.

3. The apparatus of claim 1 wherein said housing means and said mounting means are composed of a material which is immune to corrosion by said corrosion initiating substance.

4. The apparatus of claim 3 wherein said material is selected from the group consisting of: chrome plated steel, nickel plated steel, stainless steel, and plastic.

* * * * *